(12) United States Patent
Rezach et al.

(10) Patent No.: US 9,707,013 B2
(45) Date of Patent: Jul. 18, 2017

(54) SPINAL IMPLANT SYSTEM AND METHODS OF USE

(71) Applicant: Warsaw Orthopedic, Inc., Warsaw, IN (US)

(72) Inventors: William Alan Rezach, Atoka, TN (US); Jason M. May, Cordova, TN (US); Rodney R Ballard, Lakeland, TN (US); Molly K. Rice, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 57 days.

(21) Appl. No.: 14/701,231

(22) Filed: Apr. 30, 2015

(65) Prior Publication Data
US 2016/0317206 A1 Nov. 3, 2016

(51) Int. Cl.
*A61B 17/70* (2006.01)

(52) U.S. Cl.
CPC .................. *A61B 17/7037* (2013.01)

(58) Field of Classification Search
CPC .......... A61B 17/7035–17/704; A61B 17/8605–17/862; A61B 17/70
USPC .................................. 606/264–275
See application file for complete search history.

(56) References Cited

U.S. PATENT DOCUMENTS

| | | | | |
|---|---|---|---|---|
| 8,100,946 B2* | 1/2012 | Strausbaugh | ...... | A61B 17/7032 606/266 |
| 8,636,781 B2* | 1/2014 | Biedermann | ................. | 606/279 |
| 8,888,820 B2* | 11/2014 | Blain | ................. | A61B 17/7032 606/268 |
| 8,986,349 B1* | 3/2015 | German | ............. | A61B 17/7068 606/279 |
| 9,381,043 B2* | 7/2016 | Biedermann | ...... | A61B 17/7037 |
| 2004/0138660 A1* | 7/2004 | Serhan | ............... | A61B 17/7037 606/272 |
| 2005/0096653 A1* | 5/2005 | Doubler | ............. | A61B 17/7041 606/277 |
| 2006/0161152 A1* | 7/2006 | Ensign | ............... | A61B 17/7037 606/278 |
| 2006/0161153 A1* | 7/2006 | Hawkes | ............. | A61B 17/7032 606/278 |
| 2006/0200128 A1* | 9/2006 | Mueller | ............. | A61B 17/7032 606/308 |
| 2006/0276792 A1* | 12/2006 | Ensign | ............... | A61B 17/7037 606/264 |
| 2007/0088357 A1* | 4/2007 | Johnson | ............. | A61B 17/7032 606/86 A |
| 2007/0093827 A1* | 4/2007 | Warnick | ............. | A61B 17/7032 606/86 A |
| 2007/0123862 A1* | 5/2007 | Warnick | ............. | A61B 17/7032 606/261 |

(Continued)

*Primary Examiner* — Eduardo C Robert
*Assistant Examiner* — Michelle C Eckman

(57) ABSTRACT

A bone fastener comprises a first member including an inner surface defining an implant cavity and a wall defining a groove. A first element is disposed within the groove. A second member is configured to penetrate tissue and engageable with the first element to dispose the first element in a capture orientation within the groove to connect the members. A second element is engageable with the first element to urge the first element to the capture orientation. Systems, instruments and methods are disclosed.

20 Claims, 19 Drawing Sheets

(56) References Cited

U.S. PATENT DOCUMENTS

| | | | |
|---|---|---|---|
| 2007/0270832 A1* | 11/2007 | Moore | A61B 17/7011 606/278 |
| 2008/0015576 A1* | 1/2008 | Whipple | A61B 17/7037 606/60 |
| 2008/0045963 A1* | 2/2008 | Abdou | A61B 17/7032 606/86 A |
| 2008/0086129 A1* | 4/2008 | Lindemann | A61B 17/685 606/86 R |
| 2008/0108992 A1* | 5/2008 | Barry | A61B 17/7037 606/258 |
| 2008/0243193 A1* | 10/2008 | Ensign | A61B 17/7032 606/305 |
| 2008/0249570 A1* | 10/2008 | Carson | A61B 17/7038 606/264 |
| 2008/0269809 A1* | 10/2008 | Garamszegi | A61B 17/7037 606/305 |
| 2008/0294202 A1* | 11/2008 | Peterson | A61B 17/7032 606/305 |
| 2009/0069852 A1* | 3/2009 | Farris | A61B 17/7038 606/301 |
| 2009/0105771 A1* | 4/2009 | Lei | A61B 17/7037 606/313 |
| 2009/0149887 A1* | 6/2009 | Schlaepfer | A61B 17/7034 606/278 |
| 2009/0182384 A1* | 7/2009 | Wilcox | A61B 17/7032 606/305 |
| 2010/0125302 A1* | 5/2010 | Hammill, Sr. | A61B 17/7037 606/308 |
| 2010/0137918 A1* | 6/2010 | Wilcox | A61B 17/7037 606/301 |
| 2010/0145394 A1* | 6/2010 | Harvey | A61B 17/7049 606/302 |
| 2010/0152787 A1* | 6/2010 | Walsh | A61B 17/7037 606/308 |
| 2010/0160974 A1* | 6/2010 | Viker | A61B 17/866 606/301 |
| 2010/0160975 A1* | 6/2010 | Biedermann | A61B 17/7032 606/302 |
| 2010/0160976 A1* | 6/2010 | Biedermann | A61B 17/7035 606/302 |
| 2010/0168800 A1* | 7/2010 | Biedermann | A61B 17/7037 606/302 |
| 2010/0168801 A1* | 7/2010 | Biedermann | A61B 17/7037 606/302 |
| 2010/0204735 A1* | 8/2010 | Gephart | A61B 17/7037 606/264 |
| 2010/0241170 A1* | 9/2010 | Cammisa | A61B 17/7037 606/264 |
| 2010/0312288 A1* | 12/2010 | Hammill, Sr. | A61B 17/7037 606/305 |
| 2011/0009911 A1* | 1/2011 | Hammill, Sr. | A61B 17/7037 606/308 |
| 2011/0040335 A1* | 2/2011 | Stihl | A61B 17/7032 606/302 |
| 2011/0040336 A1* | 2/2011 | Hammill, Sr. | A61B 17/7037 606/305 |
| 2011/0098755 A1* | 4/2011 | Jackson | A61B 17/7008 606/305 |
| 2011/0276098 A1* | 11/2011 | Biedermann | A61B 17/7037 606/305 |
| 2012/0095516 A1* | 4/2012 | Dikeman | A61B 17/7032 606/305 |
| 2012/0109218 A1* | 5/2012 | Farris | A61B 17/7037 606/305 |
| 2012/0116462 A1* | 5/2012 | Arambula | A61B 17/7037 606/305 |
| 2012/0143266 A1* | 6/2012 | Jackson | A61B 17/7008 606/328 |
| 2012/0165874 A1* | 6/2012 | Biedermann | A61B 17/7037 606/278 |
| 2012/0172932 A1* | 7/2012 | Biedermann | A61B 17/7037 606/279 |
| 2012/0179209 A1* | 7/2012 | Biedermann | A61B 17/7037 606/305 |
| 2012/0179211 A1* | 7/2012 | Biedermann | A61B 17/7037 606/328 |
| 2012/0197314 A1* | 8/2012 | Farris | A61B 17/7037 606/305 |
| 2012/0232598 A1* | 9/2012 | Hestad | A61B 17/7037 606/305 |
| 2012/0245640 A1* | 9/2012 | Auerbach | A61B 17/7035 606/264 |
| 2013/0046345 A1* | 2/2013 | Jones | A61B 17/7037 606/266 |
| 2013/0096623 A1* | 4/2013 | Biedermann | A61B 17/844 606/279 |
| 2013/0096624 A1* | 4/2013 | Di Lauro | A61B 17/7011 606/279 |
| 2013/0103098 A1* | 4/2013 | Jackson | A61B 17/7037 606/305 |
| 2013/0123860 A1* | 5/2013 | Biedermann | A61B 17/8605 606/305 |
| 2013/0123861 A1* | 5/2013 | Biedermann | A61B 17/8605 606/305 |
| 2013/0150852 A1* | 6/2013 | Shluzas | A61B 17/7032 606/65 |
| 2013/0197586 A1* | 8/2013 | Matthis | A61B 17/7035 606/278 |
| 2013/0211458 A1* | 8/2013 | Rezach | A61B 17/7038 606/264 |
| 2013/0218207 A1* | 8/2013 | Carls | A61B 17/7035 606/278 |
| 2013/0218213 A1* | 8/2013 | Lemoine | A61B 17/7032 606/305 |
| 2013/0338716 A1* | 12/2013 | Biedermann | A61B 17/7037 606/278 |
| 2013/0338721 A1* | 12/2013 | Biedermann | A61B 17/7037 606/305 |
| 2013/0345754 A1* | 12/2013 | Doubler | A61B 17/7037 606/266 |
| 2014/0012337 A1* | 1/2014 | Biedermann | A61B 17/844 606/328 |
| 2014/0031880 A1* | 1/2014 | Biedermann | A61B 17/8605 606/305 |
| 2014/0163618 A1* | 6/2014 | Legallois | A61B 17/704 606/278 |
| 2014/0236238 A1* | 8/2014 | Ark | A61B 17/7037 606/278 |
| 2014/0257411 A1* | 9/2014 | Rezach | A61B 17/7037 606/305 |
| 2014/0321945 A1* | 10/2014 | Black | A61B 17/7037 411/383 |
| 2015/0119940 A1* | 4/2015 | Jackson | A61B 17/7076 606/266 |
| 2015/0134004 A1* | 5/2015 | Ziolo | A61B 17/7037 606/266 |
| 2015/0142059 A1* | 5/2015 | Biedermann | A61B 17/7035 606/266 |
| 2015/0173816 A1* | 6/2015 | Biedermann | A61B 17/8605 606/308 |
| 2015/0182261 A1* | 7/2015 | Lovell | A61B 17/7037 606/269 |
| 2015/0196337 A1* | 7/2015 | Biedermann | A61B 17/7037 606/305 |
| 2015/0196338 A1* | 7/2015 | Biedermann | A61B 17/7037 606/305 |
| 2015/0201972 A1* | 7/2015 | Doubler | A61B 17/7002 606/266 |
| 2015/0282844 A1* | 10/2015 | Vedula | A61B 17/7032 606/305 |
| 2015/0297266 A1* | 10/2015 | Kirschman | A61B 17/7032 606/266 |
| 2015/0320465 A1* | 11/2015 | Butler | A61B 17/8605 606/308 |
| 2016/0015429 A1* | 1/2016 | Butler | A61B 17/7035 606/278 |
| 2016/0030090 A1* | 2/2016 | Webb | A61B 17/7037 606/266 |

(56) References Cited

U.S. PATENT DOCUMENTS

| | | | |
|---|---|---|---|
| 2016/0038204 A1* | 2/2016 | Biedermann | A61B 17/8605 606/305 |
| 2016/0066958 A1* | 3/2016 | Raju | A61B 17/8883 606/270 |
| 2016/0106473 A1* | 4/2016 | Rezach | A61B 17/7032 606/265 |
| 2016/0113684 A1* | 4/2016 | Rezach | A61B 17/7032 606/278 |
| 2016/0143665 A1* | 5/2016 | Biedermann | A61B 17/7002 606/267 |
| 2016/0166288 A1* | 6/2016 | Biedermann | A61B 17/7037 606/266 |

* cited by examiner

SPINAL IMPLANT SYSTEM AND METHODS OF USE

TECHNICAL FIELD

The present disclosure generally relates to medical devices for the treatment of spinal disorders, and more particularly to a surgical implant system including a bone fastener.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs such as vertebral rods are often used to provide stability to a treated region. Rods redirect stresses away from a damaged or defective region while healing takes place to restore proper alignment and generally support the vertebral members. During surgical treatment, one or more rods and bone fasteners can be delivered to a surgical site. The rods may be attached via the fasteners to the exterior of two or more vertebral members. This disclosure describes an improvement over these prior art technologies.

SUMMARY

In one embodiment, a bone fastener is provided. The bone fastener comprises a first member including an inner surface defining an implant cavity and a wall defining a groove. A first element is disposed within the groove. A second member is configured to penetrate tissue and engageable with the first element to dispose the first element in a capture orientation within the groove to connect the members. A second element is engageable with the first element to urge the first element to the capture orientation. In some embodiments, systems, spinal constructs, instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
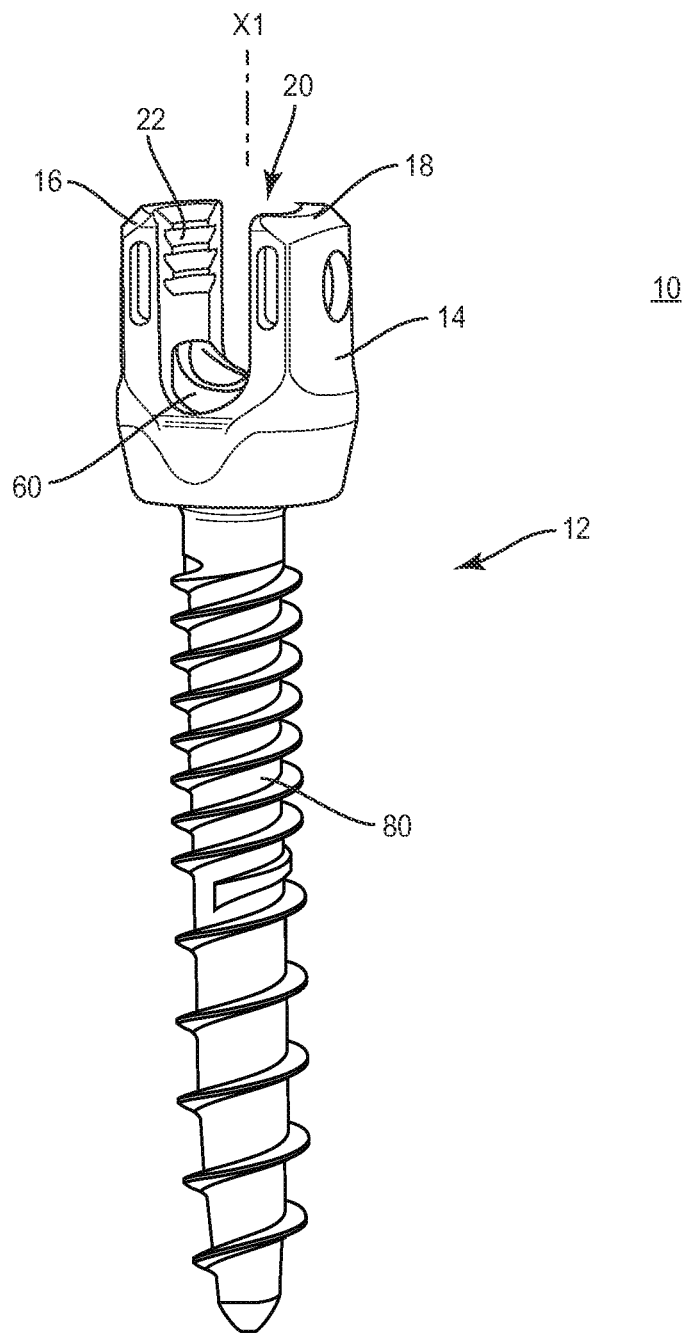
FIG. 1 is a perspective view of components of one embodiment of a spinal implant system in accordance with the principles of the present disclosure.

The exemplary embodiments of a surgical system and related methods of use disclosed are discussed in terms of medical devices for the treatment of musculoskeletal disorders and more particularly, in terms of a spinal implant system including a bone fastener. In one embodiment, the spinal implant system includes an implant comprising a bone fastener, such as, for example, a universal pedicle bone screw. In some embodiments, the spinal implant system includes a selectively coupled pedicle screw system that allows for operating room back-table assembly of a bone fastener without use of instrumentation.

In some embodiments, the spinal implant system comprises a modular system including a bone fastener including an array of members, such as, for example, receivers that can be selectively coupled to members, such as, for example, bone screw shafts. In some embodiments, the spinal implant system comprises a selectively coupled bone fastener that can be assembled on a surgical table or in-situ.

In some embodiments, the spinal implant system comprises a bone fastener that includes an auto-lock mechanism for a modular screw system. In some embodiments, the bone fastener comprises a connection between a receiver assembly and/or head and a bone screw shaft that is secure and reliable. In some embodiments, the connection between the receiver assembly and/or head and the bone screw shaft can occur on a back table, in-situ, or at a manufacturing facility. In some embodiments, the bone fastener comprises an automatic connection. In some embodiments, the bone fastener comprises a connection including a cam lock that is activated by a crown position. In some embodiments, the spinal implant system is employed with a method such that as the components of the bone fastener are assembled, the cam lock is activated to resist and/or prevent a ring from re-entering an upper chamber of a receiver to fix the receiver to the screw shaft.

In some embodiments, the spinal implant system is employed with a method that includes a step of positioning a receiver over a head of a screw shaft such that a crown is oriented in a down position allowing arms of a cam lock to splay outward. In some embodiments, the method includes the step of translating the receiver over the head of the screw shaft to contact a ring. In some embodiments, the method includes the step of translating the receiver relative to the screw shaft to apply a force to the ring and the crown to move the ring and the crown upwards such that the ring contacts a top surface of an upper chamber of the receiver and the crown is moved towards the cam lock. In some embodiments, the method includes the step of radially expanding the ring by translation of the head of the screw shaft into the receiver. In some embodiments, the method includes the step of translating the crown upwards to contact the cam lock. In some embodiments, the method includes the step of translating the receiver relative to the screw shaft to engage the cam lock with the crown causing the cam lock to translate the ring into a lower chamber such that the ring is contacting the top surface of the upper chamber. In some embodiments, the method includes the step of applying a force to the cam lock with the crown such that the cam lock continues to translate the ring into the lower chamber and the ring is translated away from the top surface of the upper chamber. In some embodiments, the method includes the step of fully inserting the head of the screw shaft into engagement with the receiver such that the cam lock is positioned to resist and/or prevent the ring from translating into the upper chamber.

In some embodiments, the spinal implant system includes a posterior pedicle screw having a receiver with a tulip head, a bone screw, a crown, a retention element and a spring configured to bias the retention element into a locked position. In some embodiments, the tulip head contains a lower chamber and an upper chamber for engagement with the retention element. In some embodiments, the retention element includes a snap ring that is prevented from opening when disposed in the lower chamber and is configured to expand when disposed in the upper chamber to facilitate radial expansion of the snap ring. In some embodiments, expansion of the snap ring allows a bone screw to be engaged within the tulip head.

In some embodiments, the snap ring is biased into the lower chamber to resist and/or prevent the retention member from unintentional migration back into the upper chamber to facilitate resisting and/or preventing disengagement of the tulip head from the bone screw. In some embodiments, the pedicle screw includes a biasing element, such as, for example, a compressible spring that applies a biasing force to the snap ring to facilitate retention of the snap ring in the lower chamber. In some embodiments, the spring is manufactured from metal, such as, for example, titanium or cobalt chrome. In some embodiments, the spring includes a compressible element, such as, for example, an O-ring. In some embodiments, the pedicle screw includes a spring to bias a snap ring retention element in a tulip head from an unlocked position, allowing for radial expansion, to a locked position in which the snap ring is prevented from expanding radially.

In some embodiments, the spinal implant system comprises a bone fastener having a tulip head and a bone screw. In some embodiments, the tulip head includes a crown, a groove having an upper chamber and a lower chamber, a snap ring and a spring. In some embodiments, the snap ring is biased into the lower chamber of the tulip head by the spring. In some embodiments, the spring is compressed by the snap ring. In some embodiments, the snap ring is configured to expand when disposed in the upper chamber. In some embodiments, the snap ring is configured to snap back into an original shape when disposed in the lower chamber. In some embodiments, the snap ring is biased into the lower chamber by the spring.

In some embodiments, the bone fastener includes a secondary retention element that is configured to prevent a primary retention element from unintentional migration back into the upper chamber. In some embodiments, the secondary retention element is configured to prevent disengagement of the tulip head from the bone screw. In some embodiments, the secondary retention element is configured for engagement with the bone screw during assembly. In some embodiments, the secondary retention element is configured to translate with the bone screw along an axis of the tulip head. In some embodiments, the secondary retention element is configured to block the primary retention element from migration into the upper chamber as the bone screw translates toward the primary retention element.

In some embodiments, the bone screw shaft is engaged with the secondary retention element. In some embodiments, the bone screw and the secondary retention element translate together to block the primary retention element from entering into the upper chamber. In some embodiments, the secondary retention element blocks a primary retention element from moving into an unlocked position or a disassembly position.

In some embodiments, the bone fastener is configured for assembly without the use of an instrument, such as, for example, a practitioner, surgeon and/or medical staff utilizes their hands for assembly. In some embodiments, the spinal implant system requires minimal force to attach a receiver and a shaft in-situ thereby reducing a pre-load on the vertebrae, such as, for, example, the pedicle.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms, "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including a bone fastener, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-9, there are illustrated components of a spinal implant system 10 including a bone fastener. In some embodiments, spinal implant system 10 includes a plurality of alternate bone fastener configurations.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Figure 2:
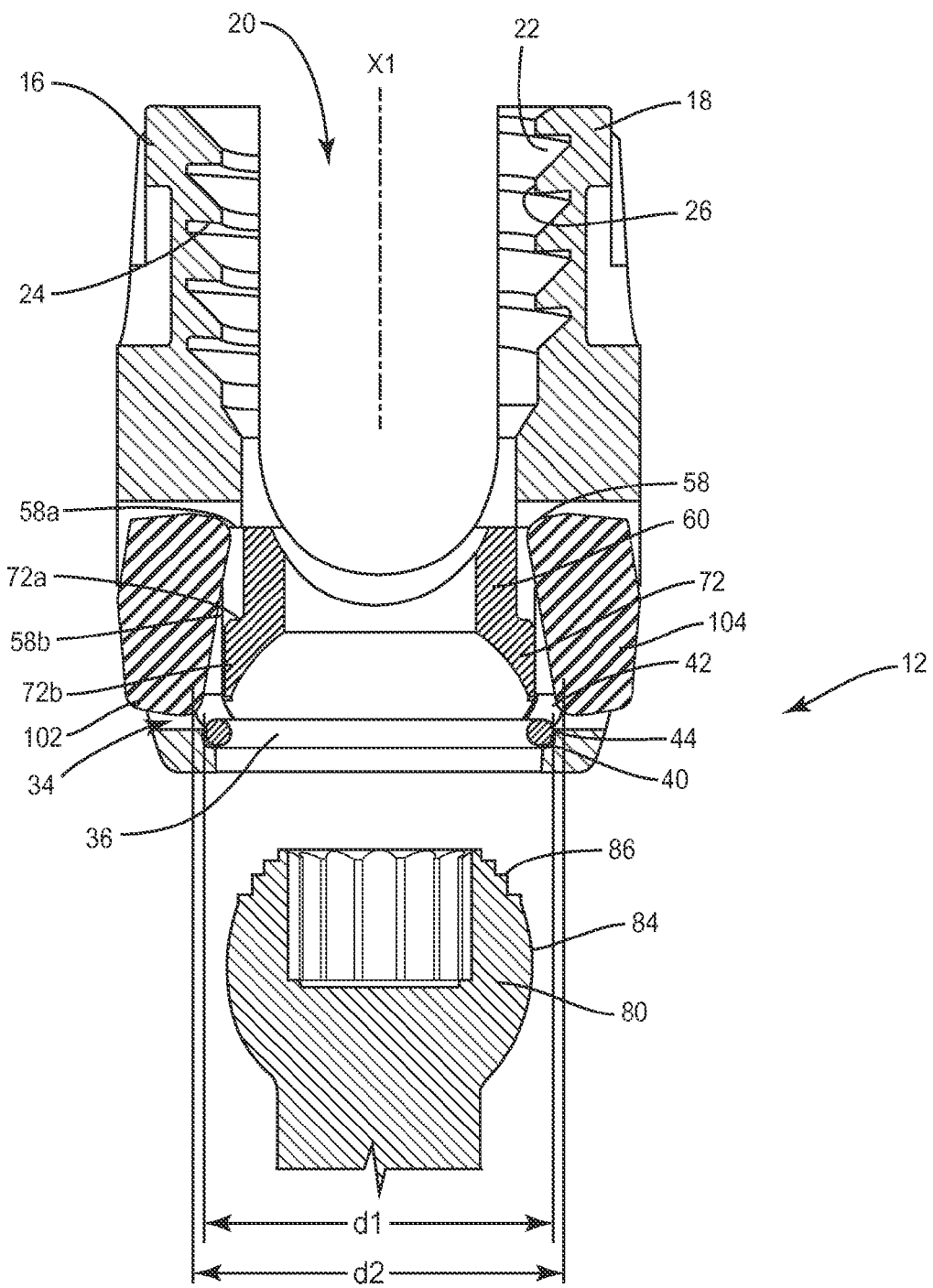
FIG. 2 is a break away cross section view of the components shown in FIG. 1.

In some embodiments, spinal implant system 10 comprises a bone fastener, such as, for example, a bone screw 12 that includes a member, such as, for example, a receiver 14 connected with a member, such as, for example, a shaft 80. Receiver 14 extends along and defines an axis X1, as shown in FIGS. 1 and 2. Receiver 14 includes a pair of spaced apart arms 16, 18 that define an implant cavity 20 therebetween configured for disposal of a component of a spinal construct, such as, for example, a spinal rod (not shown). Arms 16, 18 each extend parallel to axis X1. In some embodiments, arm 16 and/or arm 18 may be disposed at alternate orientations, relative to axis X1 such as, for example, transverse, perpendicular and/or other angular orientations such as acute or obtuse, coaxial and/or may be offset or staggered. Arms 16, 18 each include an arcuate outer surface extending between a pair of side surfaces. At least one of the outer surfaces and the side surfaces of arms 16, 18 have at least one recess or cavity therein configured to receive an insertion tool, compression instrument and/or instruments for inserting and tensioning bone screw 12. In some embodiments, arms 16, 18 are connected at proximal and distal ends thereof such that receiver 14 defines a closed spinal rod slot.

Cavity 20 is substantially U-shaped. In some embodiments, all or only a portion of cavity 20 may have alternate cross section configurations, such as, for example, closed, V-shaped, W-shaped, oval, oblong, triangular, square, polygonal, irregular, uniform, non-uniform, offset, staggered, and/or tapered. Receiver 14 includes a surface, such as, for example, a wall 22. A portion of wall 22 includes a thread form 24 located adjacent arm 16 and a thread form 26 located adjacent arm 18. Thread forms 24, 26 are each configured for engagement with a coupling member, such as, for example, a setscrew (not shown), to retain a spinal construct, such as, for example, a spinal rod (not shown) within cavity 20. In some embodiments, wall 22 may be disposed with the coupling member in alternate fixation configurations, such as, for example, friction fit, pressure fit, locking protrusion/recess, locking keyway and/or adhesive. In some embodiments, all or only a portion of wall 22 may have alternate surface configurations to enhance engagement with the spinal rod and/or the setscrew such as, for example, rough, arcuate, undulating, mesh, porous, semi-porous, dimpled and/or textured. In some embodiments, receiver 14 may include alternate configurations, such as, for example, closed, open and/or side access.

Wall 22 defines a cavity, such as, for example, a groove 34 configured for disposal of an element, such as, for example, a circumferential ring 36. Ring 36 includes a circumference that extends between ends defining an opening, such as, for example, a gap, which facilitates expansion and contraction. Groove 34 includes a portion, such as for, example, a circumferential channel 40 having a diameter d1 and a portion, such as for, example, a circumferential channel 42 having a diameter d2, as shown in FIG. 2. In some embodiments, diameter d2 is greater than diameter d1.

Channel 42 is disposed adjacent and proximal to channel 40. Channel 42 is separated from channel 40 by a protrusion, such as, for example, a lip 44. In some embodiments, shaft 80 is manually engageable with receiver 14 and/or shaft 80 is coupled with receiver 14 in a non-instrumented assembly such that ring 36 translates from and into channels 40, 42, and over lip 44, as described herein. Ring 36 is expandable and resilient between a contracted and/or capture orientation, as shown for example in FIG. 9 and an expanded orientation, as shown for example, in FIG. 5 and described herein. In some embodiments, ring 36 facilitates manual engagement of receiver 14 and shaft 80 such that receiver 14 is attached with shaft 80 in a non-instrumented assembly, as described herein.

In some embodiments, wall 22 includes a cavity, such as, for example, a slot 58 configured for disposal of a crown 60, as described herein. Slot 58 is defined by surfaces 58*a*, 58*b* of wall 22. In some embodiments, all or only a portion of surface 58*a* and/or surface 58*b* may have alternate surface configurations to enhance engagement with the spinal rod and/or the setscrew such as, for example, rough, arcuate, undulating, mesh, porous, semi-porous, dimpled and/or textured.

Figure 4:
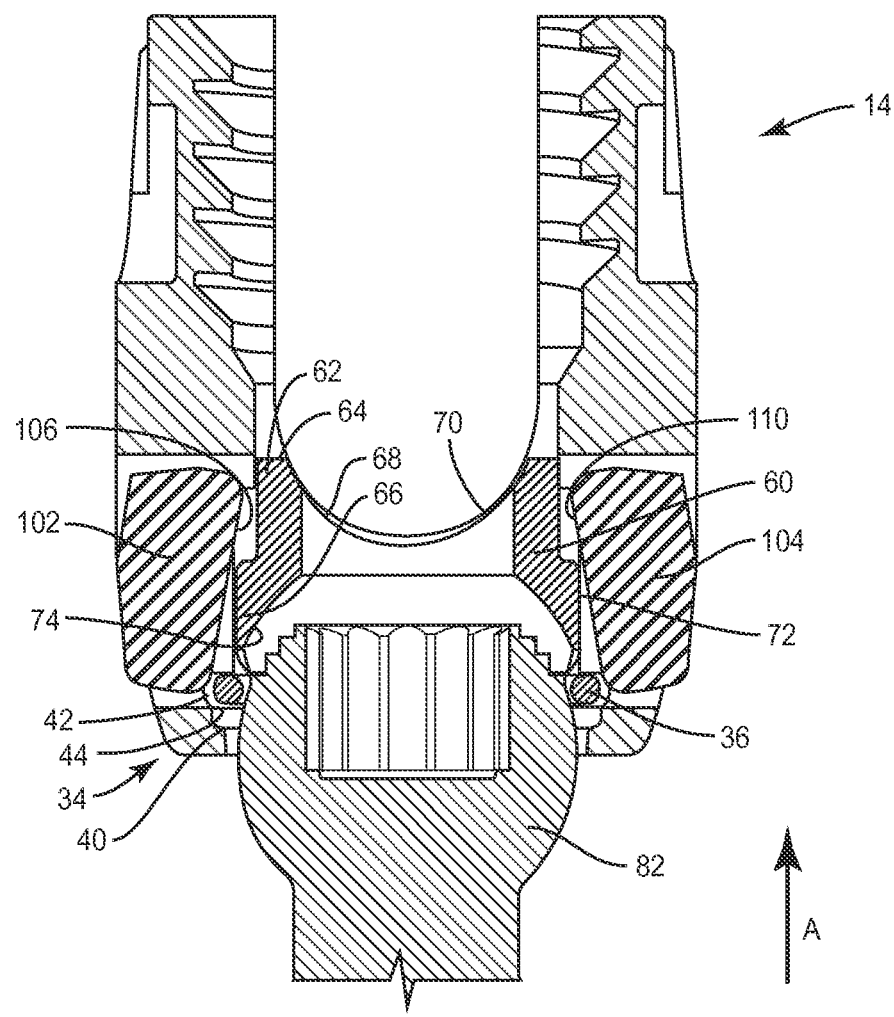
FIG. 4 is a break away cross section view of the components shown in FIG. 1.

Crown 60 is configured for disposal within cavity 20 of receiver 14. Crown 60 includes a wall 62 having an end surface 64 and an end surface 66, as shown in FIG. 4. Surface 64 is configured to define at least a portion 68 of cavity 20. Portion 68 is defined by an outer surface 70 that defines a curved portion of crown 60 configured for engagement with a spinal rod. In some embodiments, all or only a portion of surface 70 may have alternate cross section configurations, such as, for example, oval, oblong, triangular, square, polygonal, irregular, uniform, non-uniform, offset, staggered, and/or tapered.

Crown 60 includes a flange 72 configured for mating engagement with the surfaces that define slot 58 and wall 22. In some embodiments, engagement of flange 72 and the surfaces that define slot 58 and wall 22 resist and/or prevent rotation and/or axial translation of crown 60 relative to wall 22 of receiver 14. Surface 70 is disposed in fixed alignment with wall 22 for disposal of a spinal rod. Surface 66 defines an engagement portion 74 configured for engagement with head 82, as described herein.

Crown 60 is configured for engagement with an element, such as, for example, a cam lock 100, as described herein. Cam lock 100 is mounted with a portion of wall 22 and relatively movable thereabout. The outer surface of crown 60 applies a force to cam lock 100 such that cam lock 100 rotates relative to receiver 14 and into engagement with ring 36 to urge ring 36 into a capture orientation such that receiver 14 is attached with shaft 80 and prevented from disengagement therefrom, as described herein.

Cam lock 100 includes a part, such as, for example, a cam 102 and a part, such as, for example, a cam 104. Cam 104 is spaced apart from cam 102. Cam 102 includes a surface 106 configured for engagement with a shoulder of crown 60, which includes flange 72, and a surface 108 configured for engagement with ring 36. Cam 104 includes a surface 110 configured for engagement with a shoulder of crown 60, which includes flange 72, and a surface 112 configured for engagement with ring 36.

Figure 3:
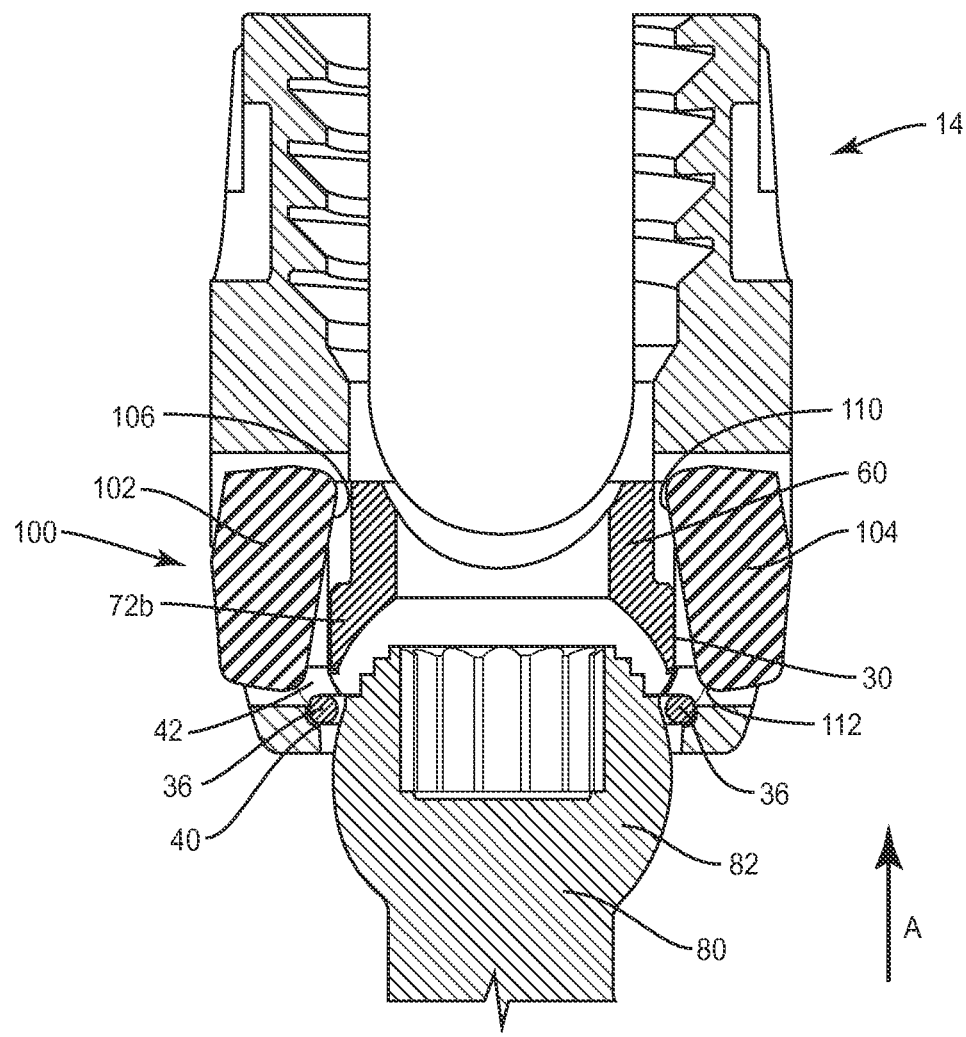
FIG. 3 is a break away cross section view of the components shown in FIG. 1.
Figure 5:
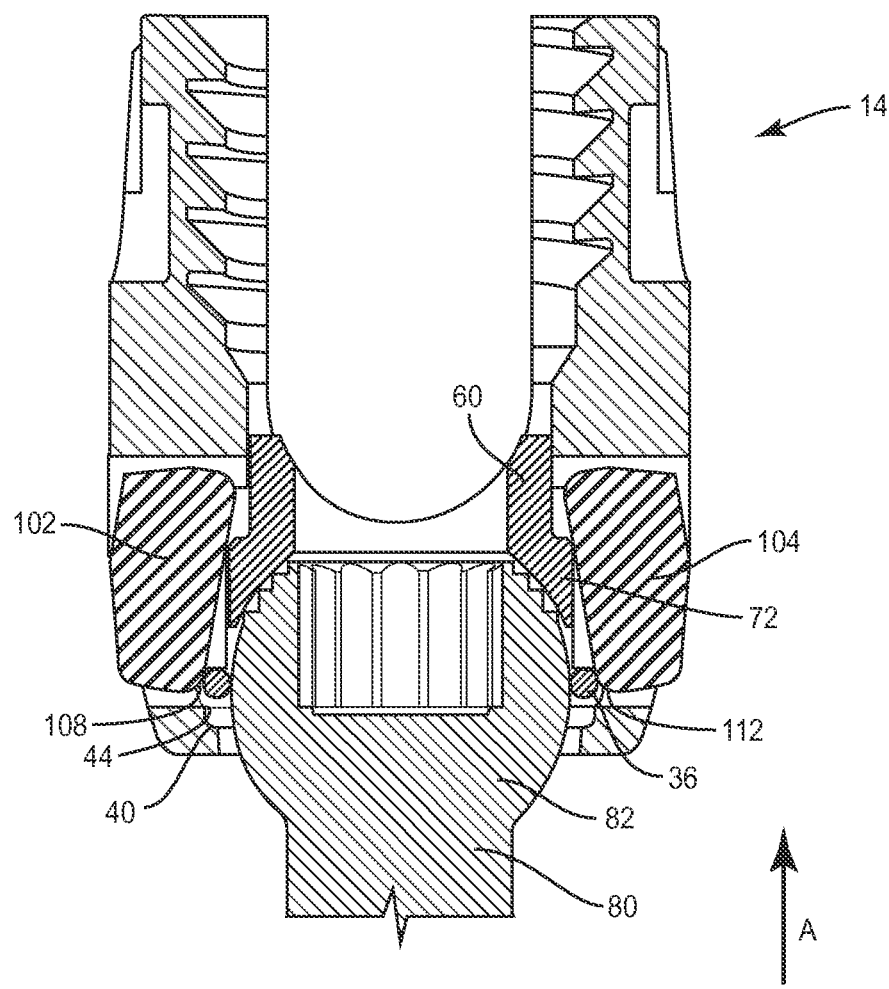
FIG. 5 is a break away cross section view of the components shown in FIG. 1.
Figure 6:
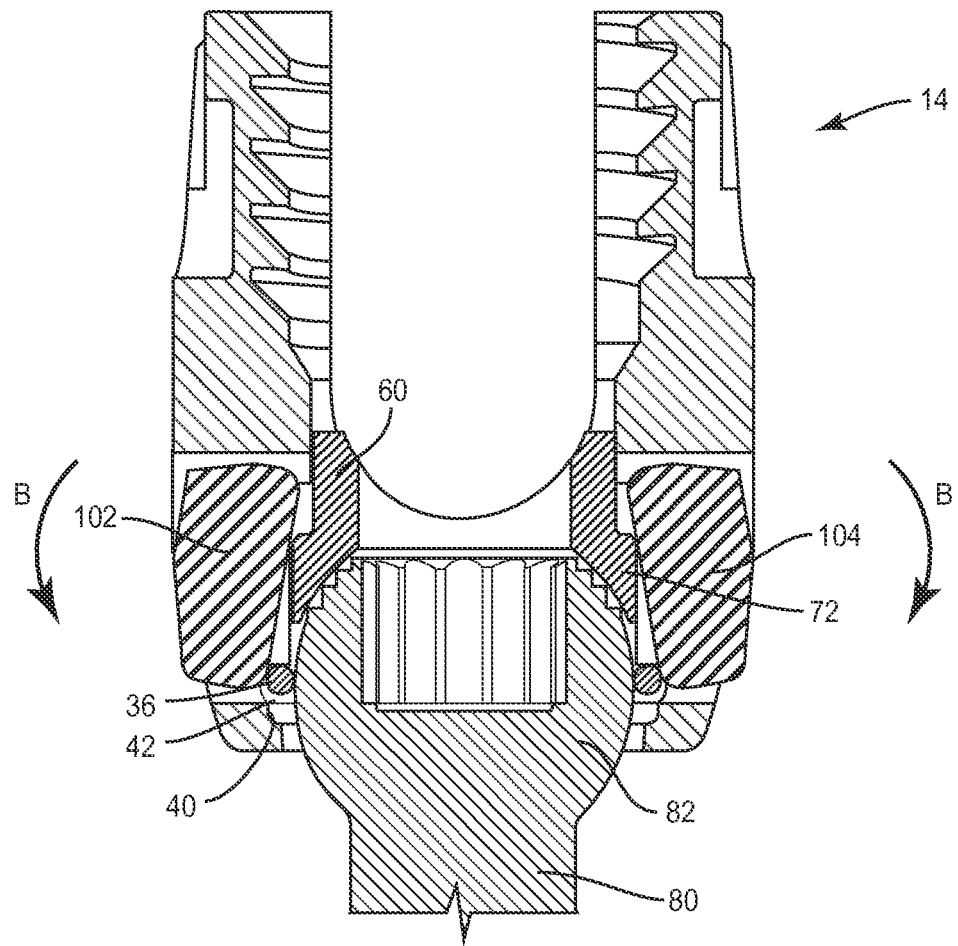
FIG. 6 is a break away cross section view of the components shown in FIG. 1.
Figure 7:
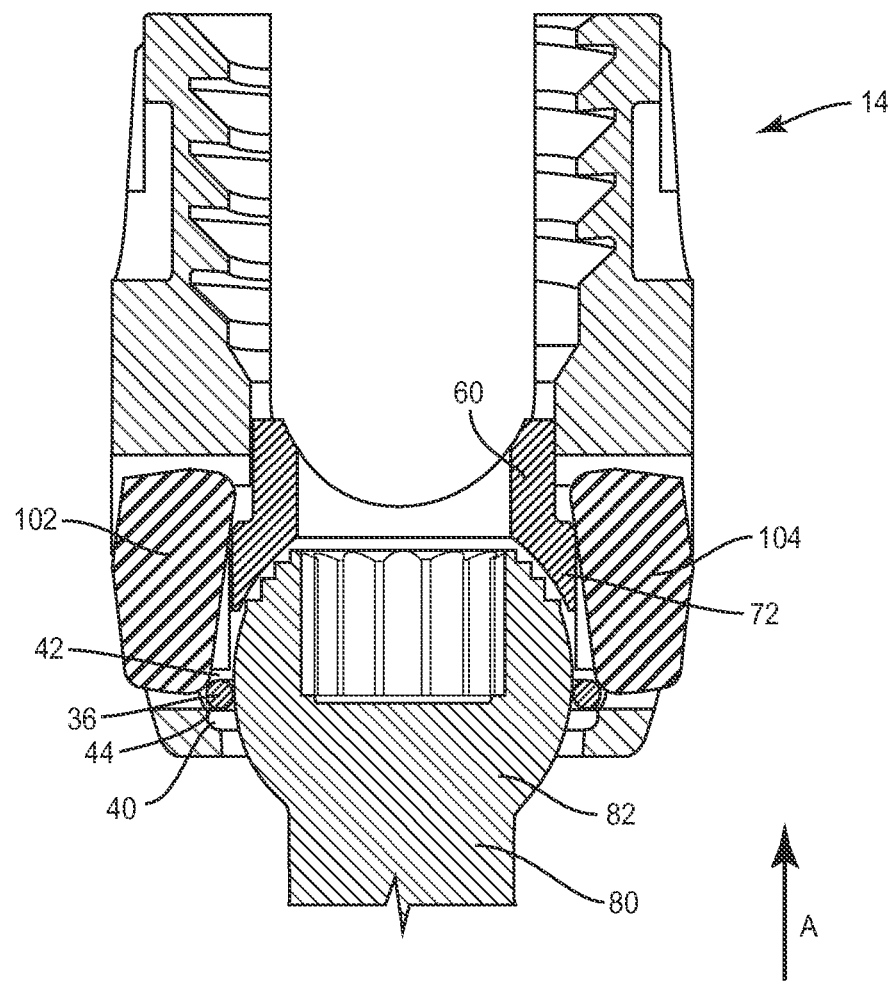
FIG. 7 is a break away cross section view of the components shown in FIG. 1.
Figure 8:
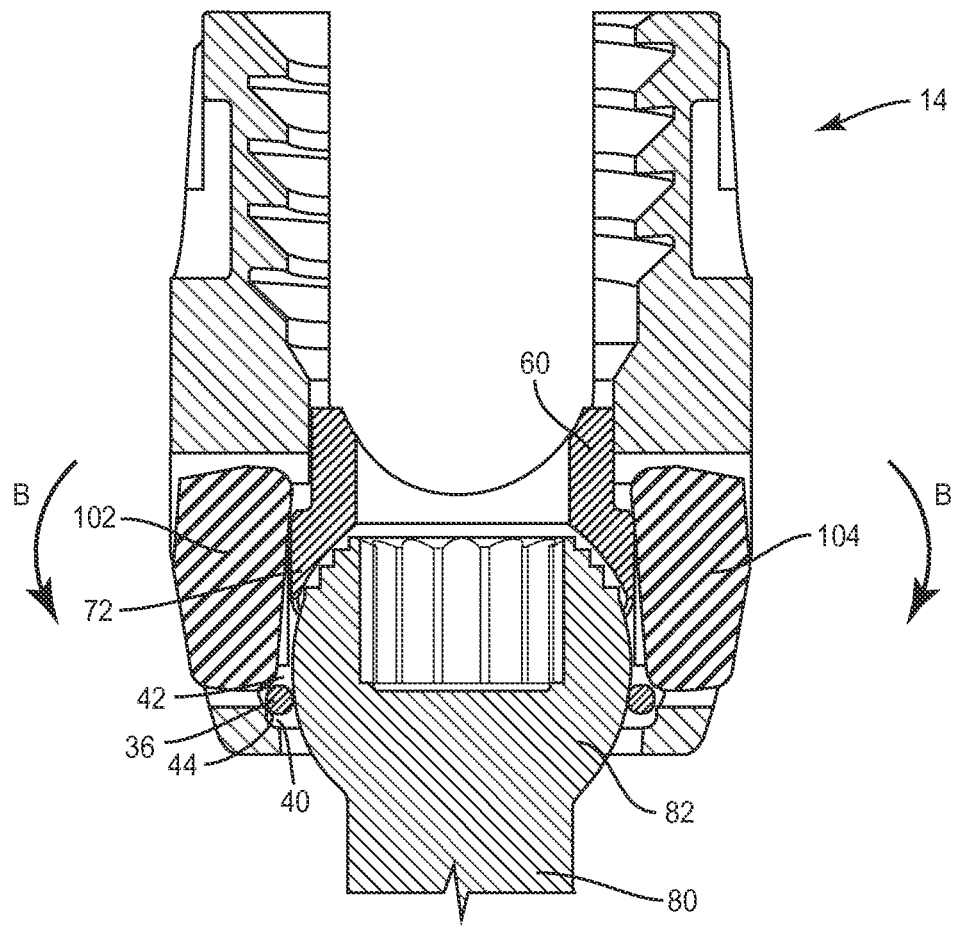
FIG. 8 is a break away cross section view of the components shown in FIG. 1.
Figure 9:
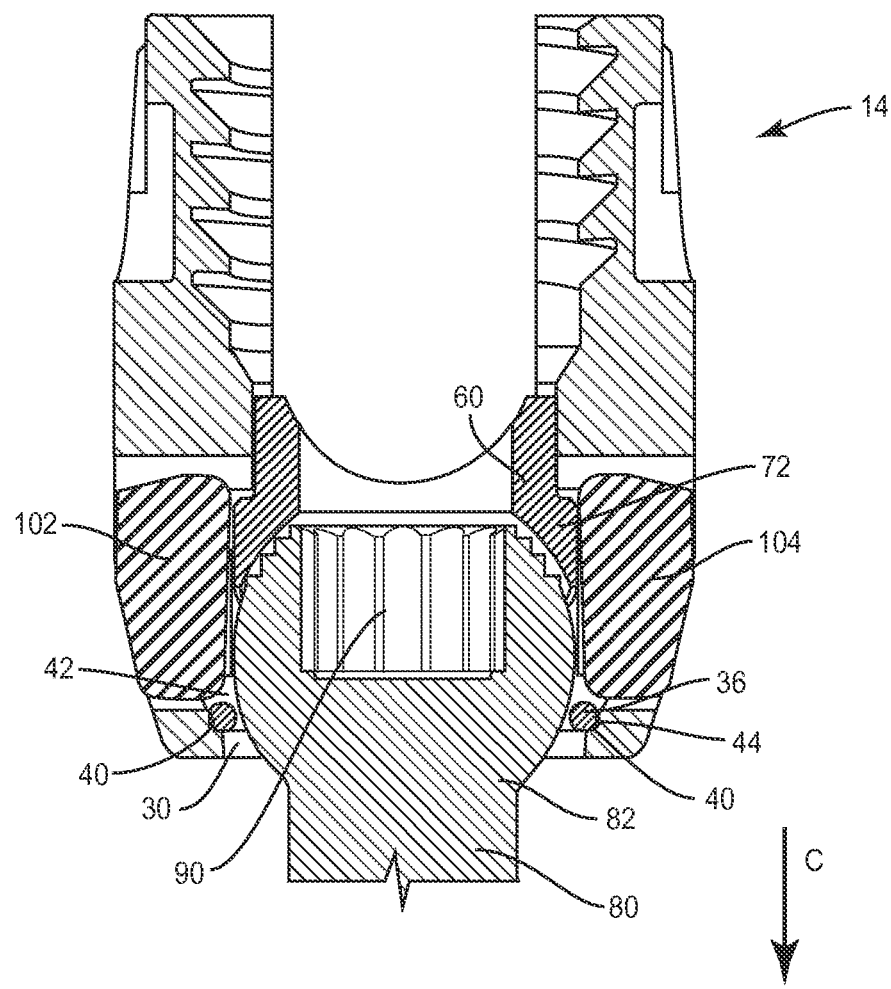
FIG. 9 is a break away cross section view of the components shown in FIG. 1.

Cams 102, 104 are rotatable relative to receiver 14 to urge ring 36 into the capture orientation. As shaft 80 is inserted into receiver 14, as shown in FIGS. 3 and 4, head 82 translates through and relative to ring 36, in the direction shown by arrow A, over lip 44 into channel 42 into an expanded orientation, as shown in FIG. 5. Head 82 engages crown 60, which translates, in the direction shown by arrow A, through slot 58 and into cavity 20. The shoulder of crown 60 translates and engages surfaces 106, 110 such that cams 102, 104 rotate, in the direction shown by arrows B in FIG. 6, relative to receiver 14. As head 82 continues to translate, in the direction shown by arrow A in FIG. 7, and cams 102, 104 rotate, in the direction shown by arrows B in FIG. 8, via engagement with crown 60, surfaces 108, 112 engage ring 36 to urge ring 36, in the direction shown by arrow C in FIG. 9, from channel 42, over lip 44 into channel 40 and relative to the surface of head 82, as shown in FIGS. 5-8, into the capture orientation, as shown in FIG. 9. Cams 102, 104 are oriented to resist and/or prevent ring 36 from moving out of channel 40. As such, cam lock 100 maintains ring 36 in the capture orientation to facilitate attachment of receiver 14 and shaft 80 for coupling and assembly of the components of bone screw 12.

Shaft 80 is configured to penetrate tissue, such as, for example, bone. Head 82 is engageable with receiver 14. Head 82 includes a substantially spherical proximal portion configured for moveable disposal with receiver 14 and crown 60. Head 82 includes a surface 84 that defines a plurality of ridges 86, as shown in FIG. 2, to improve purchase of head 82 with crown 60. Head 82 is configured to apply a force to ring 36 to move ring 36 between a contracted and/or capture orientation and an expanded orientation, as described herein. Head 82 is rotatable relative to receiver 14.

In some embodiments, head 82 is slidably engageable with a surface 30 of wall 22, as shown in FIG. 9, and movable relative thereto such that shaft 80 is rotatable along a plurality of axes relative to receiver 14 including rotation about axis X1. In some embodiments, surface 84 includes interchangeable mating surfaces, such as for example, arcuate portions and/or planar portions configured for disposal with surface 30 of any of a plurality of receivers 14 to limit rotation of receiver 14 relative to shaft 80. In some embodiments, shaft 80 is connected with a selected receiver 14 from a kit of receivers 14, as described herein, to form bone screw 12. In some embodiments, receiver 14 may be disposed with shaft 80 in alternate fixation configurations, such as, for example, friction fit, pressure fit, locking protrusion/recess, locking keyway and/or adhesive.

Head 82 includes a socket 90 having a hexalobe geometry configured for disposal of a similarly shaped bit of a tool, such as, for example, a driver (not shown) to engage the driver with head 82 to rotate shaft 80. Socket 90 is in communication with cavity 20 such that the driver may be inserted between arms 16, 18 and translated axially, until the bit of the driver is disposed in socket 90. In some embodiments, socket 90 has a cruciform, phillips, square, hexagonal, polygonal, star cross sectional configuration configured for disposal of a correspondingly shaped portion of the driver.

In some embodiments, spinal implant system 10 comprises a spinal implant kit, which includes a plurality of members, such as, for example, implant receivers 14. Receiver 14 is configured for selection from the plurality of receivers such that receiver 14 is connectable with an interchangeable member, such as, for example, shaft 80. In some embodiments, receiver 14 is configured for selection from the plurality of receivers such that receiver 14 is connectable with a compatible shaft 80.

Figure 10:
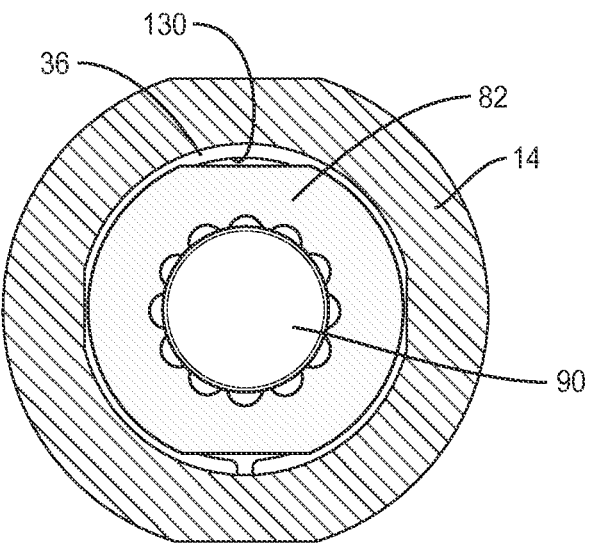
FIG. 10 is a cross section view of the components shown in FIG.
Figure 11:
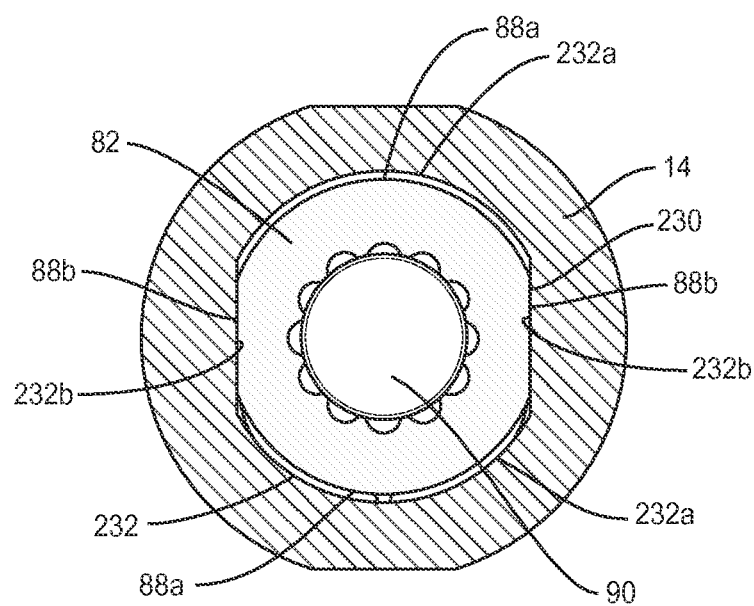
FIG. 11 is a cross section view of the components shown in FIG.
Figure 12:
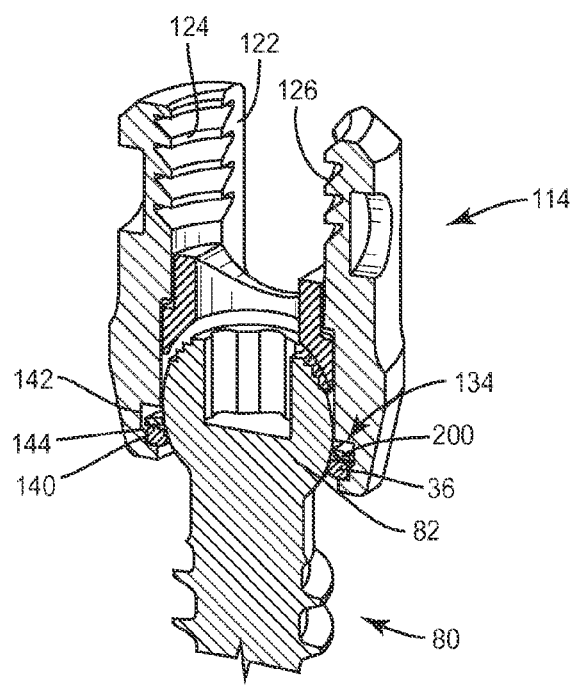
FIG. 12 is a break away cross section view of components of one embodiment of a spinal implant system in accordance with the principles of the present disclosure.

An interchangeable mating element, such as, for example, a head 82 of shaft 80 is interchangeable with a mating element, as described herein, of each of the plurality of receivers 14 to form a selected bone screw 12 having a selected movement of its components parts and/or movement relative to tissue. In some embodiments, the selected movement includes rotation and/or pivotal movement of shaft 80 relative to receiver 14 about one or a plurality of axes. In some embodiments, the selected movement includes rotation and/or pivotal movement of shaft 80 relative to receiver 14 through one or a plurality of planes. In some embodiments, shaft 80 is connected to a selected receiver 14 to comprise a multi-axial fastener, as shown in FIG. 10. In some embodiments, shaft 80 is connected to a selected receiver 14 to comprise a uniaxial fastener, as shown in FIG. 11. In some embodiments, spinal implant system 10 comprises a spinal implant kit, which includes receivers 14 and alternate receivers, such as those described herein.

A portion of surface 22 of each receiver 14 defines a particularly configured mating element, such as, for example, surface 30 configured to interface in a selective mating engagement with head 82 of shaft 80. In some embodiments, surface 30, as shown in FIG. 9, includes flat and/or arcuate surfaces to form various bone screw configurations, such as, for example, multi-axial screws, sagittal angulation screws, pedicle screws, mono-axial screws, uniplanar screws, fixed screws, anchors, tissue penetrating screws, conventional screws, expanding screws. In one embodiment, as shown in FIG. 10, head 82 is slidably engageable with a surface 130, similar to surface 30 described herein, and movable relative thereto such that shaft 80 is rotatable along a plurality of axes relative to receiver 14 including rotation about axis X1. As such, interchangeable shaft 80 is connected with a selected receiver 14 from the kit of receivers 14 to form a multi-axial bone screw 12. In one embodiment, as shown in FIG. 11, head 82 is slidably engageable with a surface 230, similar to surface 30 described herein, which includes a keyway 232 that includes mating elements, such as, for example, arcuate surfaces 232a and planar surfaces, such as, for example, flats 232b. Flats 232b are configured to interface with flats 88b of head 82 and arcuate surfaces 232a are configured to interface with arcuate surfaces 88a in a keyed connection such that shaft 80 is rotatable along a single axis and/or within a single plane relative to receiver 14. Flats 232b engage flats 88b to resist and/or prevent rotation of receiver 214 about a selected axis.

In some embodiments, manual engagement and/or non-instrumented assembly of receiver 14 and shaft 80 includes the coupling of receiver 14 and shaft 80 without use of separate and/or independent instrumentation engaged with bone fastener 12 components to effect assembly. In some embodiments, manual engagement and/or non-instrumented assembly includes a practitioner, surgeon and/or medical staff grasping receiver 14 and shaft 80 and forcibly assembling the components of bone fastener 12. In some embodiments, manual engagement and/or non-instrumented assembly includes a practitioner, surgeon and/or medical staff grasping receiver 14 and shaft 80 and forcibly snap fitting the components of bone fastener 12 together, as described herein. In some embodiments, manual engagement and/or non-instrumented assembly includes a practitioner, surgeon and/or medical staff grasping receiver 14 and shaft 80 and forcibly pop fitting the components of bone screw 12 together and/or pop fitting receiver 14 onto shaft 80, as described herein. In some embodiments, a force in a range of 2-50 N is required to manually engage receiver 14 and shaft 80 and forcibly assemble the components of bone fastener 12. For example, a force in a range of 2-50 N is required to snap fit and/or pop fit assemble receiver 14 and shaft 80. In some embodiments, a force in a range of 5-10 N is required to manually engage receiver 14 and shaft 80 and forcibly assemble the components of bone screw 12. For example, a force in a range of 5-10 N is required to snap fit and/or pop fit assemble receiver 14 and shaft 80. In some embodiments, shaft 80 is manually engaged with receiver 14 in a non-instrumented assembly, as described herein, such that removal of receiver 14 from shaft 80 requires a force and/or a pull-out strength of at least 5000 N. In some embodiments, this configuration provides manually engageable components of bone screw 12 that are assembled without instrumentation, and subsequent to assembly, the assembled components have a selected pull-out strength and/or can be pulled apart, removed and/or separated with a minimum required force.

In assembly, operation and use, spinal implant system 10, similar to the systems and methods described herein, includes a selected bone screw 12, which comprises a selected receiver 14 for connection with interchangeable shaft 80 having a selected movement, and is employed with a surgical procedure for treatment of a spinal disorder affecting a section of a spine of a patient, as discussed herein. Spinal implant system 10 is employed with a surgical procedure for treatment of a condition or injury of an affected section of the spine. In some embodiments, a selected bone screw 12 comprises a selected receiver 14 for connection with a compatible shaft 80.

The components of spinal implant system 10 include a spinal implant kit, which comprises the plurality of receivers 14 and interchangeable shafts 80. The plurality of receivers include receivers 14 and alternate receivers, such as those described herein, that interface with interchangeable shafts 80 to comprise one or more bone screw configurations. Selected bone screws 12 and one or a plurality of spinal implants, such as, for example, vertebral rods can be delivered or implanted as a pre-assembled device or can be assembled in situ. The components of spinal implant system 10 may be completely or partially revised, removed or replaced.

In some embodiments, a receiver 14 is selected from the kit of the plurality of receivers 14 for interchangeable connection with shaft 80 to comprise a bone screw 12 having a selected movement. In some embodiments, the kit of receivers 14 includes a variety of receivers having different movement configurations when assembled with an interchangeable shaft, such as, for example, multi-axial movement, sagittal angulation movement, fixed axis movement, mono-axial movement and/or uni-planar movement.

For example, the components of bone screw 12 are assembled, which includes disposing crown 60 with slot 58, cam lock 100 with wall 22, ring 36 with groove 34 and aligning head 82 with receiver 14, as described herein. Shaft 80 is inserted into receiver 14, as shown in FIGS. 3 and 4, and head 82 translates through ring 36, in the direction shown by arrow A, over lip 44 into channel 42 into an expanded orientation, as shown in FIG. 5. The shoulder of crown 60 engages cams 102, 104, which rotate in the direction shown by arrows B. Head 82 translates, in the direction shown by arrow A, and cams 102, 104 rotate, in the direction shown by arrows B in FIG. 6, via engagement with crown 60, such that surfaces 108, 112 engage ring 36 to urge ring 36, in the direction shown by arrow C in FIG. 9, from channel 42, over lip 44 into channel 42 and relative to the surface of head 82, as shown in FIGS. 5-8, into the capture orientation, as shown in FIG. 9. Cams 102, 104 resist and/or prevent ring 36 from moving out of channel 40 to maintain ring 36 in the capture orientation to facilitate attachment of receiver 14 and shaft 80 for coupling and assembly of the components of bone screw 12.

In use, for treatment of a spinal disorder, shaft 80 can be threaded and engaged with tissue. In some embodiments, the selected bone screw 12 is disposed adjacent vertebrae at a surgical site and is manipulated to drive, torque, insert or otherwise connect bone screw 12 with vertebrae.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the fixation elements with vertebrae. In some embodiments, the agent may be HA coating. In some embodiments, the agent may include one or a plurality of therapeutic agents and/or pharmacological agents for release, including sustained release, to treat, for example, pain, inflammation and degeneration.

In some embodiments, the use of microsurgical and image guided technologies may be employed to access, view and repair spinal deterioration or damage, with the aid of spinal implant system 10. The components of spinal implant system 10 can be made of radiolucent materials such as polymers. Radiomarkers may be included for identification under x-ray, fluoroscopy, CT or other imaging techniques.

In some embodiments, spinal implant system 10 can include one or a plurality of bone screws 12 such as those described herein and/or fixation elements, which may be employed with a single vertebral level or a plurality of vertebral levels. In some embodiments, bone screws 12 may be engaged with vertebrae in various orientations, such as, for example, series, parallel, offset, staggered and/or alternate vertebral levels. In some embodiments, bone screws 12 may be configured as multi-axial screws, sagittal angulation screws, pedicle screws, mono-axial screws, uni-planar screws, fixed screws, anchors, tissue penetrating screws, conventional screws, expanding screws. In some embodiments, bone screws 12 may be employed with wedges, anchors, buttons, cups, snaps, friction fittings, compressive fittings, expanding rivets, staples, nails, adhesives, posts, connectors, fixation plates and/or posts.

In one embodiment, as shown in FIGS. 12-19, spinal implant system 10, similar to the systems and methods described herein, comprises a bone screw 112, similar to bone screw 12 described herein. Bone screw 112 includes a receiver 114, similar to receiver 14 described herein, connected with shaft 80 described herein.

Figure 13:
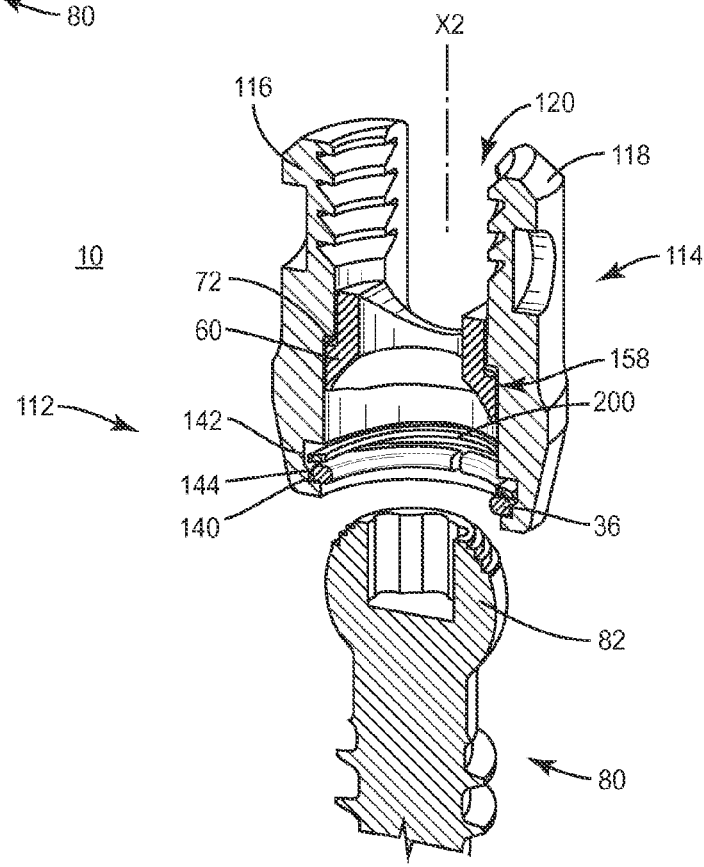
FIG. 13 is a break away cross section view of the components shown in FIG. 12.

Receiver 114 extends along and defines an axis X2, as shown in FIG. 13. Receiver 114 includes a pair of spaced apart arms 116, 118 that define an implant cavity 120 therebetween configured for disposal of a component of a spinal construct. Receiver 114 includes a wall 122, which includes thread forms 124, 126.

Wall 122 defines a groove 134 configured for disposal of ring 36 described herein. Groove 134 includes channels 140, 142, similar to channels 40, 42 described herein. Channel 142 is separated from channel 140 by a lip 144. Ring 36 is expandable and resilient between a contracted and/or capture orientation, as shown for example in FIG. 12 and an expanded orientation, as shown for example, in FIG. 17 and described herein.

Wall 122 includes a slot 158, similar to slot 58 described herein, configured for disposal of crown 60, described herein. Flange 72 of crown 60 is configured for mating engagement with the surfaces that define slot 158 and wall 122. Engagement of flange 72 and the surfaces that define slot 158 and wall 122 resist and/or prevent rotation and/or axial translation of crown 60 relative to wall 122.

Figure 20:
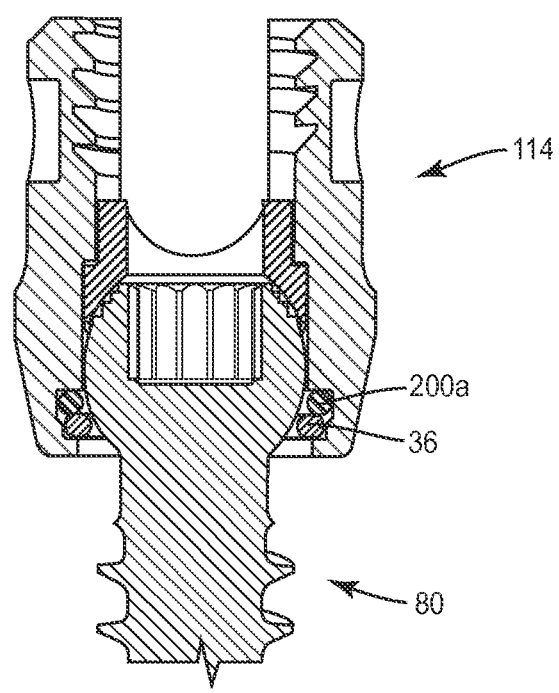
FIG. 20 is a break away cross section view of the components shown in FIG. 12.

Channel 142 is configured for disposal of an element, such as, for example, a spring 200. Spring 200 is circumferentially disposed within channel 142 and has a spring washer configuration. Spring 200 is configured to apply a biasing force to ring 36 to urge ring 36 into a capture orientation such that receiver 114 is attached with shaft 80 and resists and/or prevents disengagement therefrom, as described herein. In some embodiments, spring 200 includes materials, such as, for example, titanium and/or cobalt chrome. In some embodiments, the spring element comprises a coned-disc spring, a conical spring washer, a disc spring and/or a Belleville spring or cupped spring washer. In some embodiments, as shown in FIG. 20, the spring element includes an elastomeric O-ring 200a configured to apply a biasing force to ring 36 to urge ring 36 into a capture orientation such that receiver 114 is attached with shaft 80 and resists and/or prevents disengagement therefrom, similar to that described herein.

Figure 14:
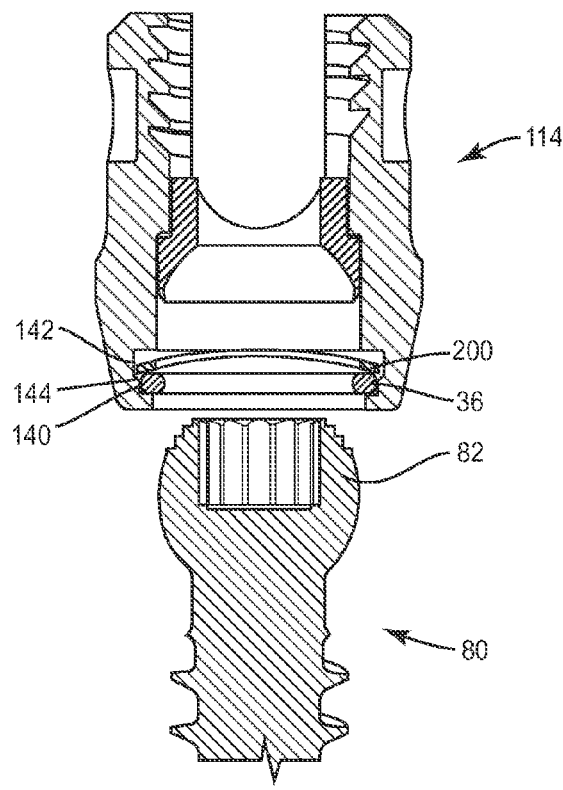
FIG. 14 is a break away cross section view of the components shown in FIG. 12.
Figure 15:
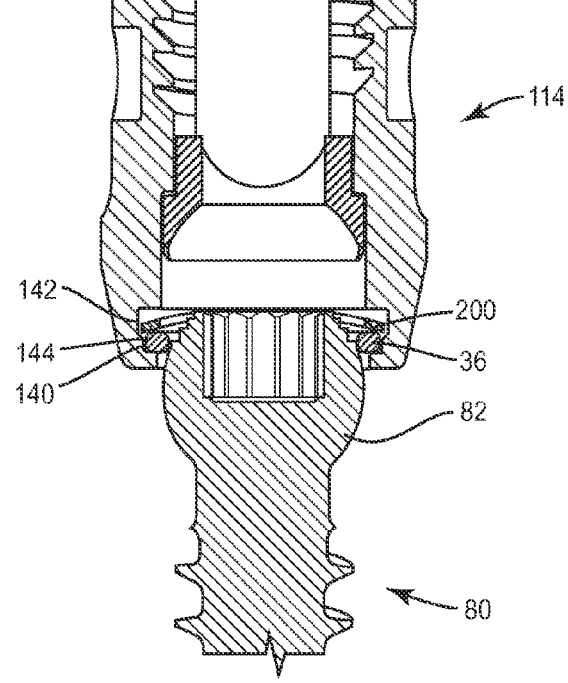
FIG. 15 is a break away cross section view of the components shown in FIG. 12.
Figure 16:
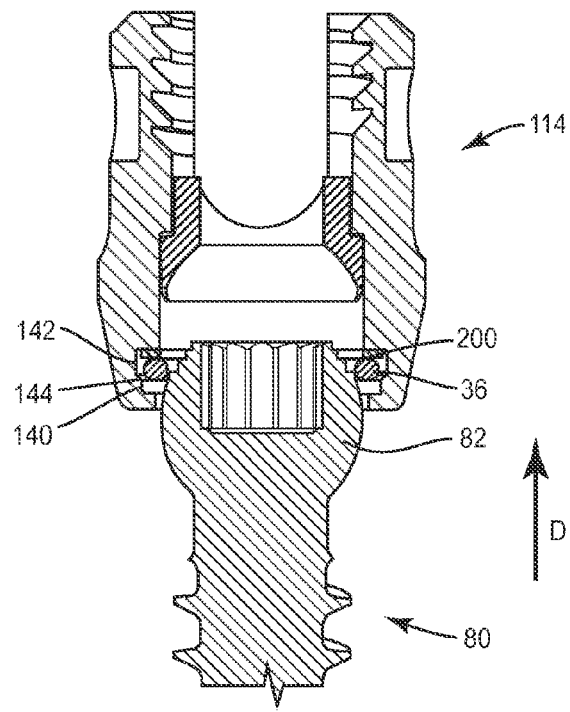
FIG. 16 is a break away cross section view of the components shown in FIG. 12.
Figure 17:
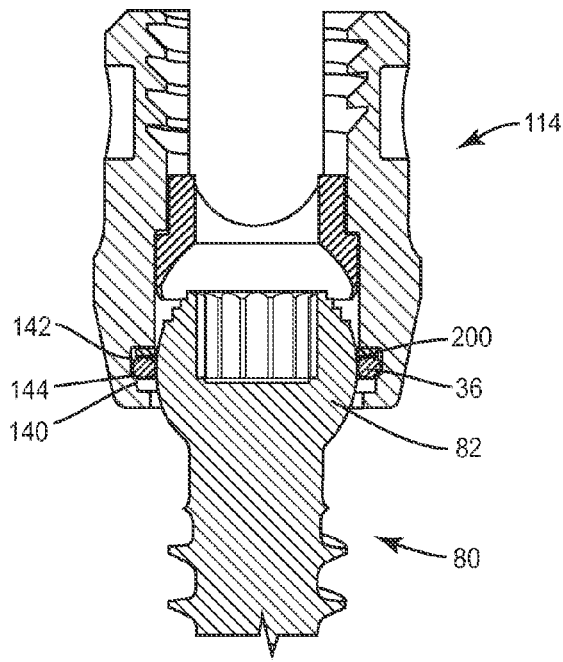
FIG. 17 is a break away cross section view of the components shown in FIG. 12.

For example, similar to the methods described herein, the components of bone screw 112 are assembled, which includes disposing crown 60 with slot 158, spring 200 with channel 142, ring 36 with groove 134 and aligning head 82 with receiver 114, as shown in FIGS. 13 and 14. Shaft 80 is inserted into receiver 114, as shown in FIG. 15. Head 82 translates through and relative to ring 36, in the direction shown by arrow D in FIG. 16, over lip 144 into channel 142 into an expanded orientation, as shown in FIG. 17.

Figure 18:
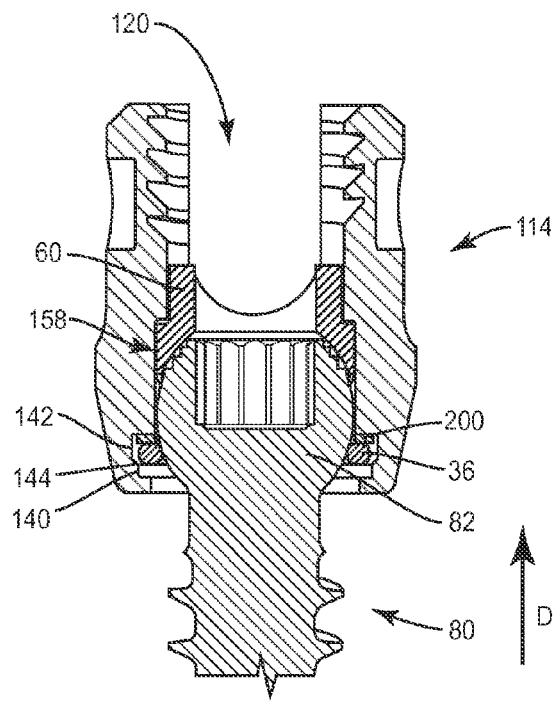
FIG. 18 is a break away cross section view of the components shown in FIG. 12.
Figure 19:
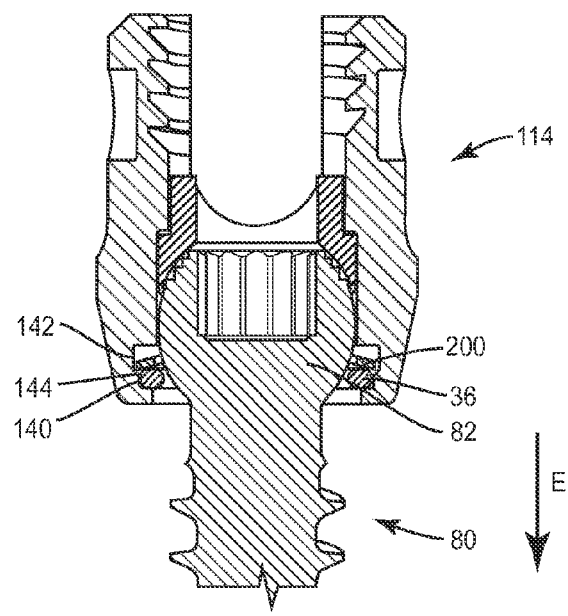
FIG. 19 is a break away cross section view of the components shown in FIG. 12.

Head 82 translates through and relative to ring 36, in the direction shown by arrow D in FIG. 18, and head 82 engages crown 60, which translates through slot 158 and into cavity 120. Spring 200 applies a biasing force, in the direction shown by arrow E in FIG. 19, to ring 36 to urge ring 36 into a capture orientation such that receiver 114 is attached with shaft 80 and resists and/or prevents disengagement therefrom.

In one embodiment, as shown in FIGS. 21-27, spinal implant system 10, similar to the systems and methods described herein, comprises a bone screw 212, similar to bone screw 12 described herein. Bone screw 212 includes a receiver 214, similar to receiver 14 described herein, connected with shaft 80 described herein.

Figure 21:
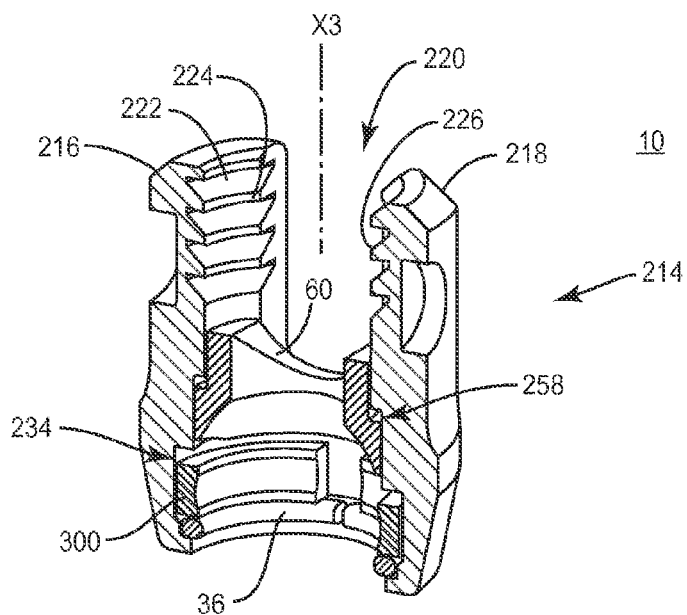
FIG. 21 is a break away cross section view of components of one embodiment of a spinal implant system in accordance with the principles of the present disclosure.
Figure 22:
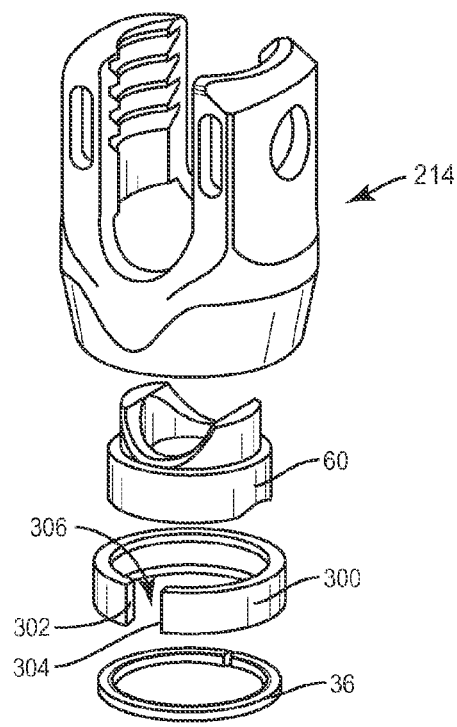
FIG. 22 is a perspective view of the components shown in FIG. 21 with parts separated.

Receiver 214 extends along and defines an axis X3, as shown in FIG. 21. Receiver 214 includes a pair of spaced apart arms 216, 218 that define an implant cavity 220 therebetween configured for disposal of a component of a spinal construct. Receiver 214 includes a wall 222, which includes thread forms 224, 226.

Wall 222 defines a groove 234 configured for disposal of ring 36 described herein. Groove 234 includes channels 240, 242, similar to channels 40, 42 described herein. Channel 242 is separated from channel 240 by a lip 244. Ring 36 is expandable and resilient between a contracted and/or capture orientation, as shown for example in FIG. 27 and an expanded orientation, as shown and described herein.

Wall 222 includes a slot 258, similar to slot 58 described herein, configured for disposal of crown 60, described herein. Flange 72 of crown 60 is configured for mating engagement with the surfaces that define slot 258 and wall 222. Engagement of flange 72 and the surfaces that define slot 258 and wall 222 resist and/or prevent rotation and/or axial translation of crown 60 relative to wall 222.

Channel 242 is configured for disposal of an element, such as, for example, a collar 300. Collar 300 is circumferentially disposed in channel 242. Collar 300 extends between an end 302 and an end 304. Ends 302, 304 define a gap 306. Gap 306 is configured to allow expansion and contraction of collar 300 during engagement with head 82.

Collar 300 is engageable with head 82 for fixation therewith such that collar 300 translates with head 82. As such, collar 300 is engageable with ring 36 to urge ring 36 into a capture orientation such that receiver 214 is attached with shaft 80 and resists and/or prevents disengagement therefrom, as described herein.

Figure 23:
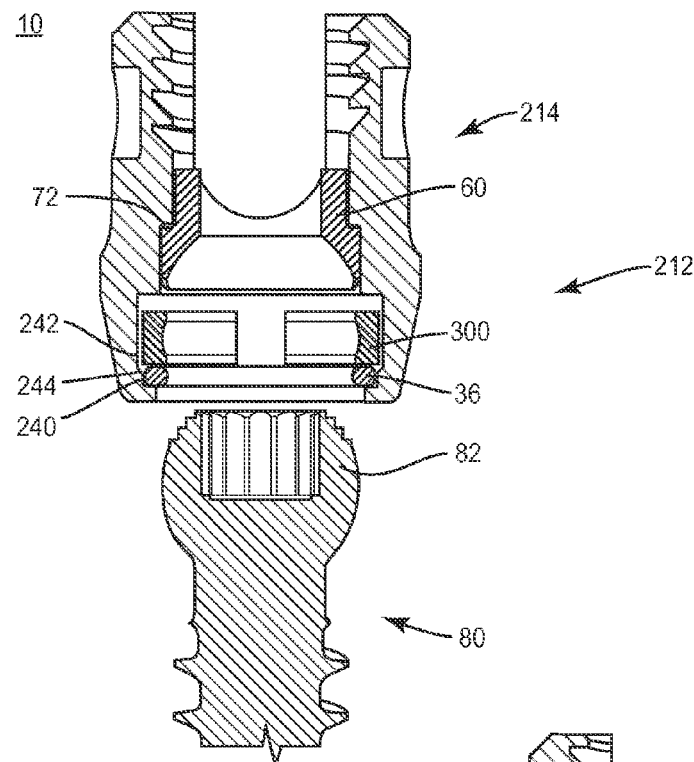
FIG. 23 is a break away cross section view of the components shown in FIG. 21.
Figure 24:
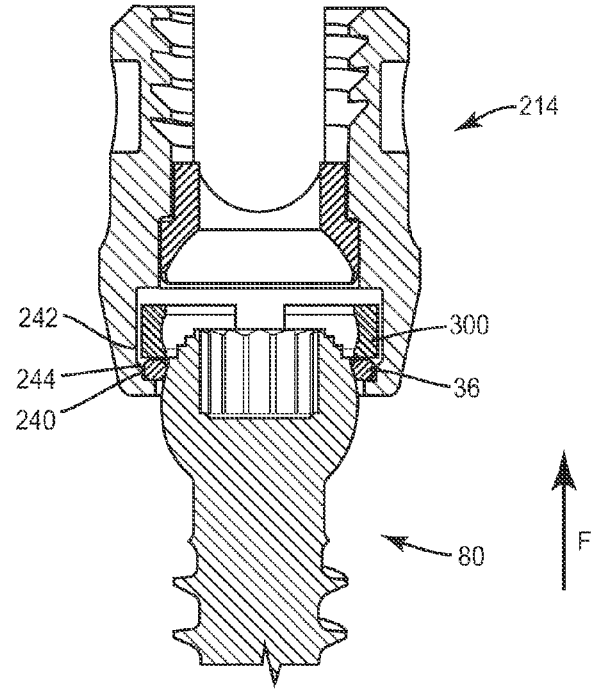
FIG. 24 is a break away cross section view of the components shown in FIG. 21.
Figure 25:
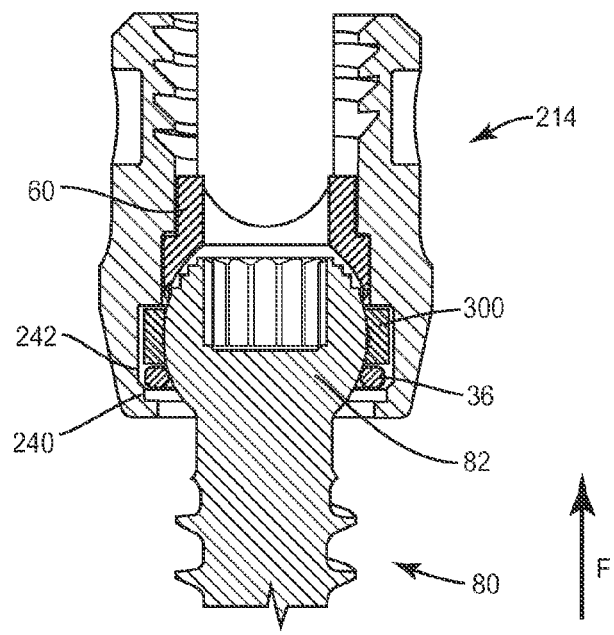
FIG. 25 is a break away cross section view of the components shown in FIG. 21.

For example, similar to the methods described herein, the components of bone screw 212 are assembled, which includes disposing crown 60 with slot 258, collar 300 with channel 242, ring 36 with groove 234 and aligning head 82 with receiver 214, as shown in FIG. 23. Shaft 80 is inserted into receiver 214, as shown in FIG. 24. Head 82 translates through and relative to ring 36, in the direction shown by arrow F in FIGS. 24 and 25, over lip 244 into channel 242 into an expanded orientation, similar to that shown and described herein.

Figure 26:
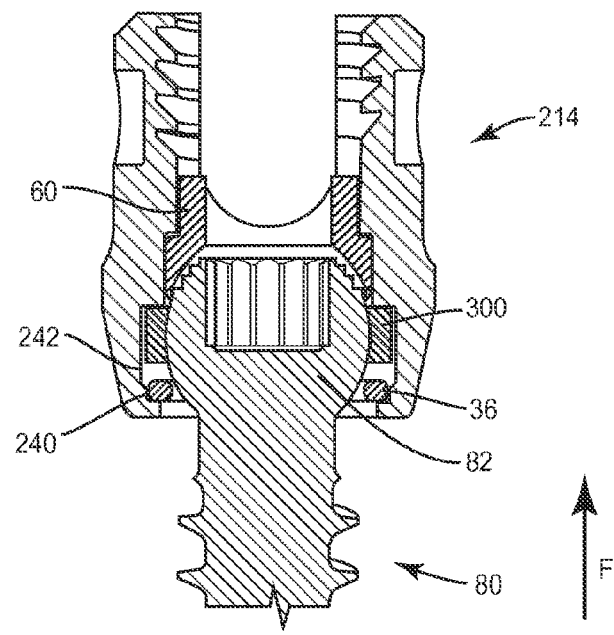
FIG. 26 is a break away cross section view of the components shown in FIG. 21.
Figure 27:
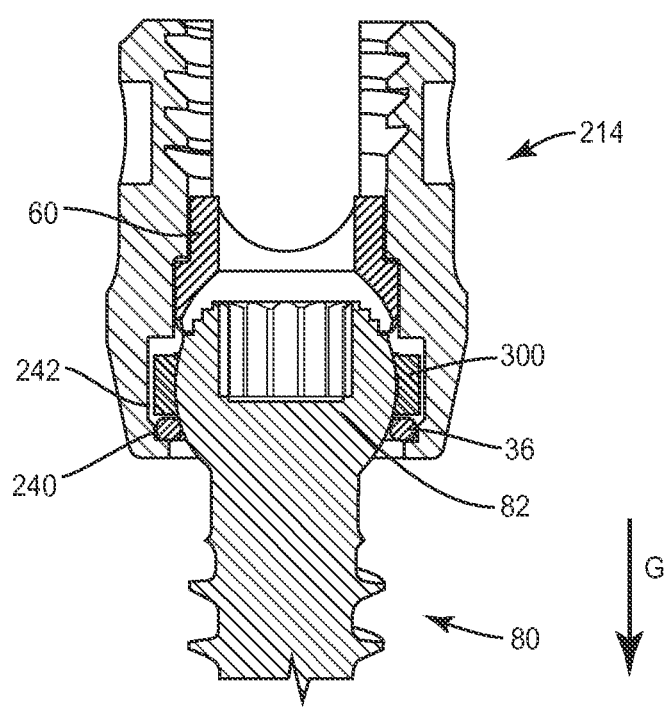
FIG. 27 is a break away cross section view of the components shown in FIG. 21.

Head 82 translates through and relative to ring 36, in the direction shown by arrow F in FIG. 26. Head 82 engages crown 60 and collar 300 engages head 82 for fixation therewith such that collar 300 translates with head 82. Collar 300 translates with head 82, in the direction shown by arrow G in FIG. 27, to apply a force to ring 36 to urge ring 36 into a capture orientation such that receiver 214 is attached with shaft 80 and resists and/or prevents disengagement therefrom. Collar 300 provides a force that blocks, resists and/or prevents ring 36 from entering channel 242.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A bone fastener comprising:
    a first member including an inner surface defining an implant cavity and a wall defining a groove;
    a first element disposed within the groove;
    a second member being configured to penetrate tissue and engageable with the first element to dispose the first element in a capture orientation within the groove to connect the members; and
    a second element engageable with the first element to urge the first element to the capture orientation, the second element comprising a first cam and a second cam spaced apart from the first cam, the cams being rotatable relative to the first member into engagement with the first element,
    wherein the groove includes a first circumferential channel and a second circumferential channel, the first element being disposed in the first circumferential channel in the capture orientation and in the second circumferential channel in an expanded orientation.

2. A bone fastener as recited in claim 1, further comprising a crown disposed with the implant cavity, the second member being engageable with the crown such that the crown engages the second element to urge the first element to the capture orientation.

3. A bone fastener as recited in claim 1, wherein the second element includes a collar disposed within the groove.

4. A bone fastener as recited in claim 3, wherein the groove includes a first circumferential channel and a second circumferential channel, the first element being disposed in the first circumferential channel and the collar being disposed in the second circumferential channel in the capture orientation.

5. A bone fastener as recited in claim 3, wherein the collar is fixed with the second member in the capture orientation.

6. A bone fastener as recited in claim 1, wherein the second element includes a circumferential collar that defines a gap and is disposed within the groove.

7. A bone fastener as recited in claim 1, wherein the second element includes a biasing member.

8. A bone fastener as recited in claim 7, wherein the groove includes a first circumferential channel and a second circumferential channel, the first element being disposed in the first circumferential channel and the biasing member being disposed in the second circumferential channel in the capture orientation.

9. A bone fastener as recited in claim 1, wherein the second element includes a spring.

10. A bone fastener as recited in claim 9, wherein the spring is circumferentially disposed in the groove.

11. A bone fastener as recited in claim 1, wherein the second element includes an elastomeric O-ring.

12. A bone fastener as recited in claim 1, wherein the first element is expandable between the capture orientation and an expanded orientation.

13. A bone fastener as recited in claim 1, wherein the second member is axially translatable relative to the first member to expand the first element.

14. A bone fastener as recited in claim 1, wherein the first element includes a circumferential ring that defines a gap.

15. A bone fastener as recited in claim 1, further comprising a crown disposed with the implant cavity and engageable with the second member.

16. A bone fastener as recited in claim 1, wherein the cams are rotatable relative to the first member to urge the first element into the capture orientation.

17. A bone fastener as recited in claim 1, a head of the second member is inserted into the first member and translates through and relative to the first element as the first element moves from the capture orientation to the expanded configuration.

18. A bone fastener as recited in claim 1, further comprising a crown disposed with the implant cavity, wherein a head of the second member engages the crown as the first element moves from the expanded orientation to the capture orientation such that a shoulder of the crown translates and engages first surfaces of the cams to rotate the cams relative to the first member and second surfaces of the cams engage the first element to urge the first element into the capture configuration.

19. A spinal implant system comprising:
- a plurality of alternate first members, each of the first members including an inner surface defining an implant cavity and a wall defining a groove;
- a first element disposed within the groove;
- a second member being configured to penetrate tissue and including a mating element engageable with a first member such that the second member is interchangeable with the plurality of first members, the second member being engageable with the first element to dispose the first element in a capture orientation within the groove to connect the members; and
- a second element engageable with the first element to urge the first element to the capture orientation, the second element comprising a first cam and a second cam spaced apart from the first cam, the cams being rotatable relative to the first member into engagement with the first element,
wherein the groove includes a first circumferential channel and a second circumferential channel, the first element being disposed in the first circumferential channel in the capture orientation and in the second circumferential channel in an expanded orientation.

20. A spinal implant system comprising:
- a plurality of alternate implant receivers, each of the implant receivers including a wall defining a groove;
- a ring disposed within the groove;
- a bone screw shaft including a head engageable with an implant receiver such that the shaft is compatible with the plurality of implant receivers, the shaft being engageable with a band to dispose the band in a capture orientation within the groove to connect the shaft with the implant receiver; and
- an element engageable with the band to urge the band to the capture orientation, the element comprising a first cam and a second cam spaced apart from the first cam, the cams being rotatable relative to the plurality of implant receivers into engagement with the ring,
wherein the groove includes a first circumferential channel and a second circumferential channel, the ring being disposed in the first circumferential channel in the capture orientation and in the second circumferential channel in an expanded orientation.

* * * * *